United States Patent
Nakano et al.

(12)

(10) Patent No.: US 6,281,313 B1
(45) Date of Patent: Aug. 28, 2001

(54) 2,2'BIS(6-BENZOTRIAZOLYLPHENOL) COMPOUND, ULTRAVIOLET RAY ABSORBER COMPRISING THE COMPOUND, COPOLYMER CONTAINING THE COMPOUND AND POLYMER COMPOSITION CONTAINING THE COMPOUND

(75) Inventors: Shinji Nakano; Emiko Daimon; Minoru Yamamoto; Mitsuo Akada, all of Itano-gun (JP)

(73) Assignee: Otsuka Chemical Co., Ltd., Osaka (JP)

(*) Notice: Subject to any disclaimer, the term of this patent is extended or adjusted under 35 U.S.C. 154(b) by 0 days.

(21) Appl. No.: 09/568,705

(22) Filed: May 11, 2000

Related U.S. Application Data

(62) Division of application No. 09/214,697, filed as application No. PCT/JP98/02030 on May 7, 1998, now Pat. No. 6,084,104.

(30) Foreign Application Priority Data

May 8, 1997 (JP) ..................................... 9-118231

(51) Int. Cl.$^7$ ......................... C08F 126/06; C07D 249/20
(52) U.S. Cl. ....................... 526/259; 526/261; 526/328.5; 526/335; 526/341; 526/344; 526/346; 546/272.4; 548/259; 548/260
(58) Field of Search ................................... 526/259, 261, 526/328.5, 335, 341, 344, 346; 546/272.4; 548/259, 260

(56) References Cited

U.S. PATENT DOCUMENTS 4,716,234 12/1987 Dunks et al. .................... 548/259

FOREIGN PATENT DOCUMENTS

| 0431868 | 6/1991 | (EP). |
| 0490815 | 9/1994 | (EP). |
| 49061071 | 6/1974 | (JP). |
| 55039180 | 3/1980 | (JP). |
| 60038411 | 2/1985 | (JP). |
| 08208628 | 8/1996 | (JP). |

*Primary Examiner*—Helen L. Pezzuto
(74) *Attorney, Agent, or Firm*—Baker Botts L.L.P.

(57) ABSTRACT

The present invention provides a 2,2'-bis(6-benzotriazolylphenol) compound represented by the formula

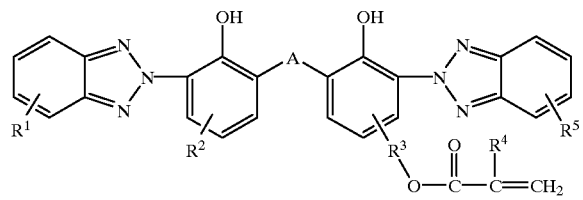

wherein A represents a methylene group or the like, $R^1$ and $R^5$ each represent a hydrogen atom, an alkyl group or the like, $R^2$ represents a hydrogen atom or the like, $R^3$ represents an alkylene group or the like, and $R^4$ represents a hydrogen atom or a methyl group.

The compound of the invention is useful as an UV absorber. Further, the compound of the invention can be incorporated into a copolymer by copolymerization with a vinyl monomer, and a polymer composition containing the copolymer can be used as an UV absorber.

6 Claims, No Drawings

2,2'BIS(6-BENZOTRIAZOLYLPHENOL) COMPOUND, ULTRAVIOLET RAY ABSORBER COMPRISING THE COMPOUND, COPOLYMER CONTAINING THE COMPOUND AND POLYMER COMPOSITION CONTAINING THE COMPOUND

This is a divisional of application Ser. No. 09/214.697 filed Jan. 8, 1999, now U.S. Pat. No. 6,084,104 which is a 371 of PCT/JP98/02030 filed May 7, 1998.

TECHNICAL FIELD

The present invention relates to a 2,2'-bis(6-benzotriazolylphenol) compound, an ultraviolet ray absorber consisting of the compound, and a copolymer and a polymer composition containing the compound.

BACKGROUND ART

Among a large number of UV absorbers, a benzotriazole-type UV absorber which is transparent to visible light is used most widely in terms of amounts and applications. However, conventional UV absorbers involve various problems to be solved. For example, the conventional benzotriazole-type UV absorbers have the following drawbacks.

(1) They are high in vapor pressures because of the low molecular weights. When a conventional UV absorber is blended with a resin and molded, it tends to volatilize, so that the yield is decreased or the contamination of mold or the pollution of working environment occurs. Further, the absorber bleeds out of the surface of molded article or coating film with the lapse of time to impair the appearance of the product. it is washed out by rain or water containing a detergent or the like in using environment, failing to impart UV absorption to products over a long period of time.

(2) The benzotriazole-type compound has inherently a property to react with a wide variety of metal ions(metal ion reactivity). For this reason, it easily forms chelate compounds with metal ions, so that color formation occurs, impairing an inherent transparency to visible light and losing properties as UV absorber.

Accordingly, in order to alleviate the defects indicated in (1) and (2) above, namely, volatility, elution, reactivity with metal ions and the like, a method has been usually employed in which a bulky substituent is introduced in the molecule of UV absorber, especially, in an adjacent carbon atom having a phenolic hydroxyl group.

However, the bulky substituent to be introduced in the method is usually a tert-butyl group, a tert-octyl group or a dimethylbenzyl group. The introduction of such a substituent incapable of UV absorption lowers the molecular absorption coefficient in proportion to increased molecular weight of the UV absorber, with the result that UV absorption per molecule is reduced.

Another method is known in which 2-hydroxyphenylbenzotriazole group is introduced as bulky group (Japanese Unexamined Publication No. 49-61,071, Japanese Examined Patent Publication No. 55-39,180 and the like).

Although the compounds disclosed in these documents exhibit improved properties concerning volatility, elution, etc., but the effects achieved are still unsatisfactory. Further, these documents does not teach the importance of metal ion resistance.

Japanese Unexamined Patent Publication No.60-38,411 discloses an approach in which polymerizable unsaturated group $(CH_2=C(R^a)COO(R^b)-)$ (wherein $R^a$ is a hydrogen atom or a methyl group, and $R^b$ is a linear or branched alkylene group having 2 to 10 carbon atoms) is introduced into the molecule of UV absorber to convert it into a copolymer and to improve the properties relating to volatility and elution.

However, the polymerizable UV absorber described in the document has a defect that it does not sufficiently absorb UV and has a high volatility itself, so that it is volatilized when the graft polymerization reaction is conducted, for example, in an extruder or a kneading molding machine.

Accordingly, a UV absorber has not been found yet which can eliminate the defects associated with the, conventional UV absorber, namely, which is free from volatility and elution problems during polymerization or molding, which is excellent in alkali resistance, heat resistance and metal ion resistance and which has a high absorptivity. Consequently, it is desired to provide UV absorbers having been improved in these properties.

DISCLOSURE OF INVENTION

It is an object of the present invention to provide, by solving various problems associated with the prior art as discussed above, novel 2,2'-bis(6-benzotriazolylphenol) compounds which do not volatilize during high-temperature processing nor bleed out of the surface of a molded article, which have high weatherability and high heat resistance for a long period of time, which are not colored in an atmosphere where alkalis or metal ions are present, and which have a high molecular absorption coefficient and excellent UV absorptivity.

Another object of the present invention is to provide a UV absorber which eliminates the defects associated with the conventional UV absorbers, namely, which is free from volatilization and elution during polymerization or molding, which is excellent in alkali resistance, heat resistance and metal ion resistance and which has high UV absorptivity.

Still another object of the present invention is to provide a copolymer comprising the above-mentioned 2,2'-bis(6-benzotriazolylphenol) compound as a copolymerizable component.

Another object of the present invention is to provide a polymer composition comprising the above-mentioned copolymer containing the 2,2'-bis(6-benzotriazolylphenol) compound.

Other features of the present invention will be apparent from the following description.

The present invention provides a 2,2'-bis(6-benzotriazolylphenol) compound represented by the formula

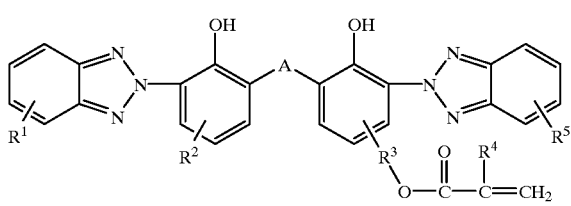

(1)

wherein
A represents a single bond, a methylene group, —CH(CH$_3$)—, —C(CH$_3$)$_2$— or —C(CH$_3$)(C$_2$H$_5$)—,
R$^1$ and R$^5$ are the same or different, and each represents a hydrogen atom, an alkyl group having 1 to 4 carbon atoms, an aryl group, an alkoxy group having 1 to 4 carbon atoms or a halogen atom,
R$^2$ represents a hydrogen atom or an alkyl group having 1 to 8 carbon atoms,
R$^3$ represents a single bond or a linear or branched alkylene group having 1 to 6 carbon atoms, and
R$^4$ represents a hydrogen atom or a methyl group.

The 2,2'-bis(6-benzotriazolylphenol) compound of formula (1) is a novel compound which has not been disclosed in literature.

The 2,2'-bis(6-benzotriazolylphenol) compound of the present invention having a high molecular absorption coefficient is excellent in UV absorption markedly low in vapor pressure, high in heat stability, and excellent in alkali resistance and metal ion resistance. Accordingly, it is useful as a UV absorber.

In the compound of the present invention, a molecule of ultraviolet-absorbable group is introduced into a carbon atom adjacent a carbon atom having a substituent phenolic hydroxyl group. This compound does not form chelate compound nor is colored even in environment where alkali metal ions, alkaline earth metal ions such as calcium or the like, or metal ions such as iron, copper or the like are present.

Further, the substituent on the carbon atom adjacent the carbon atom having the phenolic hydroxyl substituent group in the compound of the present invention is not a mere bulky substituent such as a tert-butyl group, a tert-octyl group, a dimethylbenzyl group or the like, but an ultraviolet-absorbable group per se. Accordingly, the compound of the invention has a high molecular absorption coefficient, providing a highly excellent UV absorptivity.

The present invention provides a UV absorber comprising the above-mentioned 2,2'-bis(6-benzotriazolylphenol) compound of formula (1).

The 2,2'-bis(6-benzotriazolylphenol) compound of formula (1) of the present invention has a feature that it has a highly reactive addition-polymerizable group in the molecule. As a result, the compound of the present invention can be homopolymerized or copolymerized with an addition-polymerizable monomer to introduce the ultraviolet-absorbable groups into the side chains of the resulting polymer at a desired ratio.

The present invention provides a copolymer comprising a 2,2'-bis(6-benzotriazolylphenol) compound of formula (1) as a copolymerizable component in an amount of 0.01 to 70% by weight and having a weight average molecular weight of 2,000 to 1,000,000.

The present invention provides a copolymer comprising a 2,2'-bis(6-benzotriazolylphenol) compound of formula (1) and a vinyl monomer, the amount of 2,2'-bis(6-benzotriazolylphenol) compound as the copolymerizable component being in the range of 0.01 to 70% by weight, and the copolymer having a weight average molecular weight of 2,000 to 1,000,000.

The preferable copolymers of the invention include a copolymer comprising a 2,2'-bis(6-benzotriazolylphenol) compound of formula (1) and a vinyl monomer, the amount of 2,2'-bis(6-benzotriazolylphenol) compound as the copolymerizable component being in the range of 0.01 to 30% by weight, the copolymer having a weight average molecular weight of 2,000 to 1,000,000, and a copolymer comprising a 2,2'-bis(6-benzotriazolylphenol) compound of formula (1) and a vinyl monomer, the amount of 2,2'-bis(6-benzotriazolylphenol) compound as the copolymerizable component being in the range of 0.05 to 70% by weight, the copolymer having a weight average molecular weight of 2,000 to 1,000,000.

The polymer capable of UV absorption of the present invention has a very low vapor pressure, is not volatilized by heating during molding, and does not lose UV absorptivity. Nor does the compound of the invention as the UV absorber bleed out of the molded article formed of the polymer. Accordingly, satisfactory weatherability can be imparted to the molded product over a long period of time, so that excellent UV absorption can be achieved for a long period of time. The compound of the invention has a very low vapor pressure and a high decomposition temperature. Consequently, even when it is polymerized at high temperatures, it is not volatilized or decomposed during the reaction, making it possible to produce a UV-absorbing polymer with a required molecular weight at a remarkably high yield.

Further, the present invention provides a polymer composition comprising the above copolymer, especially a coating composition comprising the above copolymer.

Examples of the alkyl groups having 1 to 4 carbon atoms in the above formula (1) include methyl, ethyl, n-propyl, isopropyl, n-butyl, isobutyl and tert-butyl groups.

Examples of the aryl groups include phenyl, naphthyl group and the like wherein the phenyl ring may have a substituent or substituents such as an alkyl group having 1 to 4 carbon atoms, an alkoxy group having 1 to 4 carbon atoms or a halogen atom.

Examples of the alkoxy groups having 1 to 4 carbon atoms include methoxy, ethoxy, n-propoxy, isopropoxy, n-butoxy and tert-butoxy groups.

Examples of the halogen atoms include fluorine, chlorine, bromine and iodine atoms.

Examples of the alkyl groups having 1 to 8 carbon atoms include methyl, ethyl, n-propyl, isopropyl, n-butyl, isobutyl, tert-butyl, n-pentyl, n-hexyl, n-heptyl, n-octyl and tert-octyl groups.

Examples of the linear or branched alkylene groups having 1 to 6 carbon atoms include methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups.

Specific examples of 2,2'-bis(6-benzotriazolylphenol) compounds represented by formula (1) of the present invention include the following compounds.

6-(2H-benzotriazol-2-yl)-4-methacryloyloxyethyl-2-[3'-(2H-benzotriazol-2-yl)-2'-hydroxyphenyl]methylphenol 6-(2H-benzotriazol-2-yl)-4-acryloyloxyethyl-2-[3'-(2H-benzotriazol-2-yl)-2'-hydroxyphenyl]methylphenol 6-(2H-benzotriazol-2-yl)-4-methacryloyloxyethyl-2-[3'-(2H-benzotriazol-2-yl)-2'-hydroxy-5'-methylphenyl]methylphenol 6-(2H-benzotriazol-2-yl)-4-methacryloyloxyethyl-2-[3'-(2H-benzotriazol-2-yl)-2'-hydroxy-5'-methylphenyl]-α-methylmethylphenol 6-(2H-benzotriazol-2-yl)-4-methacryloyloxyethyl-2-[3'-(2H-benzotriazol-2-yl)-2'-hydroxy-5'-methylphenyl]-α,α-dimethylmethylphenol 6-(2H-benzotriazol-2-yl)-4-methacryloyloxyethyl-2-[3'-(2H-benzotriazol-2-yl)-2'-hydroxy-5'-methylphenyl]-α-ethyl-α-methylmethylphenol 6-(5-chloro-2H-benzotriazol-2-yl)-4-methacryloyloxyethyl-2-[3'-(2H-benzotriazol-2-yl)-2'-hydroxy-5'-methylphenyl]methylphenol 6-[2H-benzotriazol-2-yl)-4-methacryloyloxyethyl-2-[3-(5-chloro-2H-benzotriazol-2-yl)-2'-hydroxy-5'-methylphenyl]methylphenol 6-(2H-benzotriazol-2-yl)-4-acryloyloxyethyl-2-[3'-(2H-benzotriazol-2-yl)-2'-hydroxy-5'-methylphenyl]methylphenol 6-(2H-benzotriazol-2-yl)-4-acryloyloxyethyl-2-[3'-(2H-benzotriazol-2-yl)-2'-hydroxy-5'-methylphenyl]-α-methylmethylphenol 6-(2H-benzotriazol-2-yl)-4-acryloyloxyethyl-2-[3'-(2H-benzotriazol-2-yl)-2'-hydroxy-5'-methylphenyl]-α,α-dimethylmethylphenol 6-(2H-benzotriazol-2-yl)-4-methacryloyloxypropyl-2-[3'-(2H-benzotriazol-2-yl)-2'-hydroxy-5'-methylphenyl]methylphenol 6-(2H-benzotriazol-2-yl)-4-acryloyloxypropyl-2-[3'-(2H-benzotriazol-2-yl)-2'-hydroxy-5'-methylphenyl]methylphenol 6-(2H-benzotriazol-2-yl)-4-methacryloyloxyethyl-2-[3'-(2H-benzotriazol-2-yl)-2'-hydroxy-5'-ethylphenyl]methylphenol 6-(2H-benzotriazol-2-yl)-4-methacryloyloxyethyl-2-[3'-(2H-benzotriazol-2-yl)-2'-hydroxy-5'-n-propylphenyl]methylphenol 6-(2H-benzotriazol-2-yl)-4-methacryloyloxyethyl-2-[3'-(2H-benzotriazol-2-yl)-2'-hydroxy-5'-isopropylphenyl]methylphenol 6-(2H-benzotriazol-2-yl)-4-methacryloyloxyethyl-2-(3'-(2H-benzotriazol-2-yl)-2'-hydroxy-5'-n-butylphenyl]methylphenol 6-(2H-benzotriazol-2-yl)-4-methacryloyloxyethyl-2-[3'-(2H-benzotriazol-2-yl)-2'-hydroxy-5'-isobutylphenyl]methylphenol 6-(2H-benzotriazol-2-yl)-4-methacryloyloxyethyl-2-[3'-(2H-benzotriazol-2-yl)-2'-hydroxy-5'-tert-butylphenyl]methylphenol 6-(2H-benzotriazol-2-yl)-4-methacryloyloxyethyl-2-[3'-(5-chloro-2H-benzotriazol-2-yl)- 2'-hydroxy-5'-tert-butylphenyl]methylphenol 6-(2H-benzotriazol-2-yl)-4-methacryloyloxyethyl-2-[3'-(5-chloro-2H-benzotriazol-2-yl)-2'-hydroxy-5'-tert-butylphenyl]-α-methylmethylphenol 6-(2H-benzotriazol-2-yl)-4-methacryloyloxyethyl-2-[3'-(5-chloro-2H-benzotriazol-2-yl)-2'-hydroxy-5'-tert-butylphenyl]-α,α-dimethylmethylphenol 6-(2H-benzotriazol-2-yl)-4-methacryloyloxypropyl-2-[3'-(2H-benzotriazol-2-yl)-2'-hydroxy-5'-tert-butylphenyl]methylphenol 6-(2H-benzotriazol-2-yl)-4-acryloyloxypropyl-2-[3'-(2H-benzotriazol-2-yl)-2'-hydroxy-5'-tert-butylphenyl]methylphenol 6-(5-chloro-2H-benzotriazol-2-yl)-4-methacryloyloxypropyl-2-[3'-(2H-benzotriazol-2-yl)-2'-hydroxy-5'-tert-butylphenyl]methylphenol 6-(2H-benzotriazol-2-yl)-4-acryloyloxypropyl-2-[3'-(5-chloro-2H-benzotriazol-2-yl)-2'-hydroxy-5'-tert-butylphenyl]methylphenol 6-(2H-benzotriazol-2-yl)-4-methacryloyloxyethyl-2-[3'-(2H-benzotriazol-2-yl)-2'-hydroxy-5'-n-amylphenyl]methylphenol 6-(2H-benzotriazol-2-yl)-4-methacryloyloxyethyl-2-[3'-(2H-benzotriazol-2-yl)-2'- hydroxy-5'-sec-amylphenyl]methylphenol 6-(2H-benzotriazol-2-yl)-4-methacryloyloxyethyl-2-[3'-(2H-benzotriazol-2-yl)-2'-hydroxy-5'-tert-amylphenyl]methylphenol 6-(2H-benzotriazol-2-yl)-4-methacryloyloxyethyl-2-[3'-(2H-benzotriazol-2-yl)-2'-hydroxy-5'-isoamylphenyl]methylphenol 6-(2H-benzotriazol-2-yl)-4-methacryloyloxyethyl-2-[3'-(2H-benzotriazol-2-yl)-2'-hydroxy-5'-sec-isoamylphenyl]methylphenol 6-(2H-benzotriazol-2-yl)-4-methacryloyloxyethyl-2-[3'-(2H-benzotriazol-2-yl)-2'-hydroxy-5'-n-octylphenyl]methylphenol 6-(2H-benzotriazol-2-yl)-4-methacryloyloxyethyl-2-[3'-(2H-benzotriazol-2-yl)-2'-hydroxy-5'-tert-octylphenyl]methylphenol The 2,2'-bis(6-benzotriazolylphenol) compound of the invention has a high molecular absorption coefficient, a high UV absorptivity, a very low vapor pressure and a high heat stability. Accordingly, it is useful as an addition-type UV absorber in various resins including engineering plastics, which are required to be molded at a high temperature.

The compound of the invention can be produced, for example, by a method shown by the following reaction scheme-1 or reaction scheme-2.

Reaction scheme-1

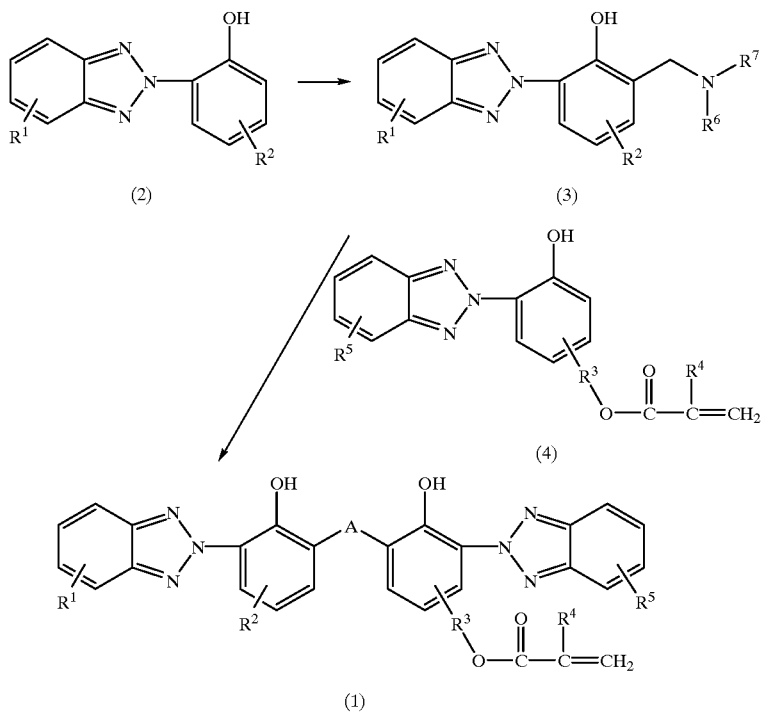

wherein A, $R^1$, $R^2$, $R^3$, $R^4$ and $R^5$ are as defined above, and $R^6$ and $R^7$ are the same or different, and each represents a hydrogen atom or an alkyl group having 1 to 8 carbon atoms, or $R^6$ and $R^7$ may form a ring in combination with each other.

In the reaction represented by the scheme-1, the compound of the invention represented by the formula (1) is produced by reacting a 2-benzotriazolylphenol compound represented by formula (2) with an amine compound and a formaldehyde derivative in a solvent to form a Mannich base compound represented by the formula (3) and then reacting the resulting compound with a compound represented by the formula (4).

The Mannich base compound represented by the formula (3) can be produced by reacting the 2-benzotriazolylphenol compound represented by the formula (2) in a solvent in the presence of 1 to 3 equivalents each of an amine compound and a formaldehyde derivative for 1 to 30 hours.

Preferable examples of the amine compounds used in the above reaction include primary amines such as monomethylamine, monoethylamine, monopropylamine, monobutylamine, monoamylamine and monohexylamine; secondary amines such as dimethylamine, diethylamine, di-n-propylamine, di-isopropylamine, di-n-butylamine, di-tert-butylamine, di-isobutylamine, diamylamine, dihexylamine, ethylmethylamine, methylisopropylamine and ethylisopropylamine; and cyclic amines such as morpholine, piperidine and pyrrolidine.

Preferable examples of the formaldehyde derivatives used in the above reaction include formaldehyde, its aqueous solution; linear oligomers such as paraformaldehyde; and cyclic oligomers such as trioxane and tetraoxymethylene.

Examples of the solvents used in the above reaction include alcohols such as methanol, ethanol, isopropanol, n-propanol, n-butanol, isobutanol and tert-butanol; aliphatic hydrocarbons such as petroleum ether, hexane and heptane; aromatic hydrocarbons such as benzene, toluene and xylene; ethers such as diethyl ether, dibutyl ether, tetrahydrofuran and dioxane; and esters such as ethyl acetate, propyl acetate and butyl acetate. These solvents can be used singly or in combination of two or more. The amount of solvent is not limited, and selected from a wide range, as required, depending on the ease of stirring, reaction temperature and solubility of the substrates. Generally, it is preferable to use the solvent in an amount of 50 to 500% based on the weight of 2-benzotriazolylphenol compound represented by the formula (2).

The reaction temperature is suitably selected from a range of 20 to 200° C., preferably 30 to 150° C., depending on the type of the solvent.

The reaction between the Mannich base compound represented by the formula (3) and the 2-benzotriazolylphenol compound represented by the formula (4) is conducted in an appropriate solvent in the presence of an alkali catalyst.

Examples of the alkali catalysts used in the reaction include alkali metal alkoxides such as sodium methoxide, sodium ethoxide, sodium n-propoxide and sodium isopropoxide; and inorganic bases such as sodium hydroxide, potassium hydroxide, sodium carbonate and potassium carbonate. These catalysts may be used singly or in combination of two or more. The amount of the alkali catalyst is not limited. It is preferably 0.01 to 10% by weight relative to the amount of the Mannich base compound represented by the formula (3).

Examples of the solvents used in the reaction include alcohols such as methanol, ethanol, isopropanol, n-propanol, n-butanol, isobutanol and tert-butanol; aliphatic hydrocarbons such as petroleum ether, hexane and heptane; aromatic hydrocarbons such as benzene, toluene and xylene; ethers such as diethyl ether, dibutyl ether, tetrahydrofuran and dioxane; and esters such as ethyl acetate, propyl acetate and butyl acetate. These solvents may be used singly or as a mixture of two or more, depending on the purpose. Further, the amount of the solvent is not limited, and can be selected depending on the ease of stirring, reaction temperature and solubility of the substrate. In general, it is preferably between 50 and 500% relative to the weight of the Mannich base compound represented by the formula (3).

The proportion of the Mannich base compound of formula (3) and the 2-benzotriazolylphenol compound of formula (4) is not limited. Usually, it is advisable that the latter is used in an amount of 0.5 to 2 mols per mol of the former.

The temperature of the reaction is suitably selected from the range of 20 to 200° C., preferably 30 to 150° C., depending on the type of the solvent. Usually, the reaction is completed in 1 to 100 hours.

2-benzotriazolylphenol compound represented by the formula (2) is reacted with the amine compound and the formaldehyde derivative to form the Mannich base compound represented by the formula (3).

The reaction between the Mannich base compound represented by the formula (5) and the 2-benzotriazolylphenol compound represented by the formula (2) is conducted under the similar reaction conditions as used in the reaction between the Mannich base compound of the formula (3) and the 2-benzotriazolylphenol compound of the formula (4).

The 2-benzotriazolylphenol compound represented by the formula (2) and used as the starting material in the above reaction scheme-1 is a known compound and easily obtainable.

Further, the 2-benzotriazolylphenol compound represented by the formula (4) which is used as the starting

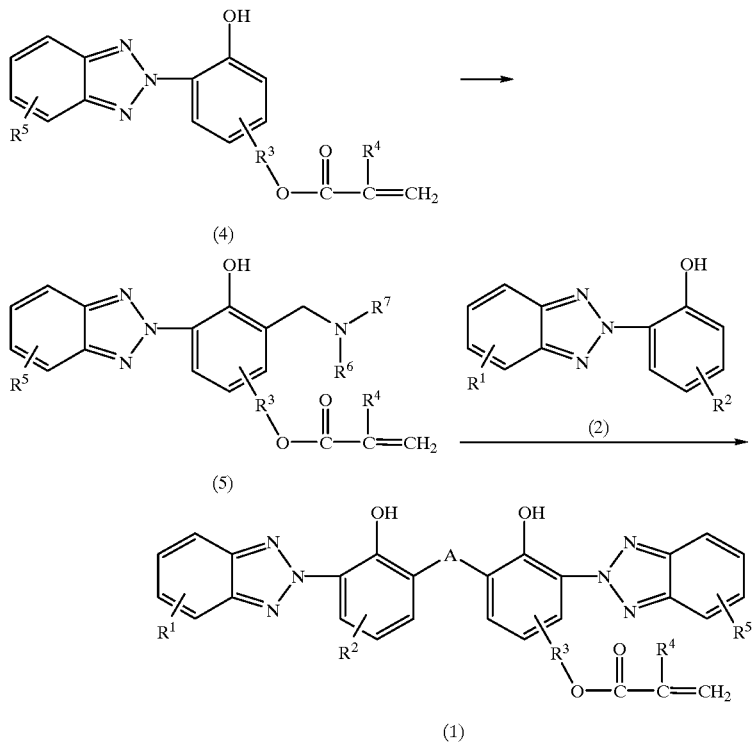

wherein A, $R^1$, $R^2$, $R^3$, $R^4$, $R^5$, $R^6$ and $R^7$ are as defined above, and $R^8$ represents a linear or branched hydroxyalkyl group having from 1 to 6 carbon atoms.

In the reaction represented by the scheme-2, the compound of the present invention represented by formula (1) can easily be produced by reacting a 2-benzotriazolylphenol compound represented by the formula (4) with an amine compound and a formaldehyde derivative in a solvent to form a Mannich base compound represented by the formula (5) and then reacting the resulting Mannich base compound with a 2-benzotriazolylphenol compound represented by the formula (2).

The reaction wherein the 2-benzotriazolylphenol compound represented by the formula (4) is reacted with the amine compound and the formaldehyde derivative in the solvent to form the Mannich base compound represented by the formula (5) is conducted under the similar reaction conditions as used in the reaction wherein the material in the above reaction scheme-1 is easily produced, for example, by the method (reaction scheme-3 below) described in Japanese Unexamined Patent Publication No.60-38,411.

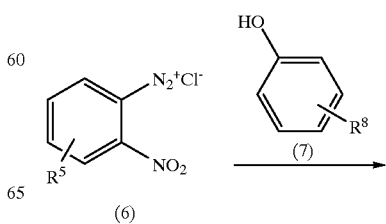

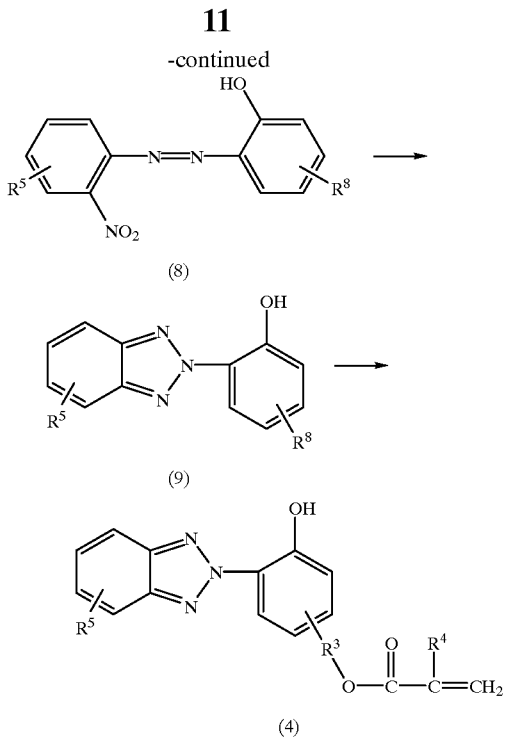

wherein $R^3$, $R^4$, $R^5$ and $R^8$ are as defined above.

In the reaction expressed by the scheme-3, the 2-benzotriazolylphenol compound represented by the formula (4) is easily produced by subjecting a diazonium salt represented by the formula (6) which is formed by the reaction of a known o-nitroaniline compound and sodium nitrite with a known hydroxyalkylphenol represented by the formula (7) to azo coupling under basic conditions to form a 2-[(2-nitrophenyl)azo]hydroxyalkylphenol compound represented by the formula (8), and then reducing the formed compound under basic conditions to form a hydroxyalkyl-2-benzotriazolylphenol compound represented by the formula (9), and finally esterifying the compound with acrylic acid or methacrylic acid.

Each of the desired compounds obtained according to the above reaction schemes-1, -2 and -3 can easily be isolated from the reaction mixture and purified according to conventional isolation and purification procedures.

The 2,2'-bis(6-benzotriazolylphenol) compound of the present invention of the formula (1) is useful as an UV. absorber.

The UV absorber comprising the 2,2'-bis(6-benzotriazolylphenol) compound of the formula (1) of the invention can be used, as required, in combination with other additives such as light stabilizer, antioxidant, plasticizer, flame retardant, antistatic agent, filler, pigment, coloring agent and the like.

The 2,2'-bis(6-benzotriazolylphenol) compound of the formula (1) of the invention can be incorporated into a polymer at a suitable stage during the production of polymer, and also before or during the molding of polymer in a usual manner.

The compound (1) of the present invention can be added to the polymer by simply dissolving the same in the polymer. It is preferable to copolymerize the compound (1) of the invention with a copolymerizable comonomer to introduce the compound into side chains of the polymer. Thus, a copolymer containing the compound (1) of the invention as a copolymer component is obtained with desired copolymerization compositions and required molecular weight. The copolymer has high level-weatherability since the UV absorptivity is not lost through elution or evaporation.

The copolymerizable comonomer is not limited so long as it can polymerize with the compound (1) of the present invention. Examples thereof include vinyl monomers such as styrene, methylstyrene, an acrylate ester, a methacrylate ester, acrylamide, acrylonitrile, methacrylonitrile, vinyl acetate, vinylidene chloride, vinyl chloride, ethylene, propylene, butadiene, isoprene, octene, decene and dodecene. Specific examples of the acrylate esters include methyl acrylate, ethyl acrylate, propyl acrylate and butyl acrylate. Specific examples of the methacrylate esters include methyl methacrylate, ethyl methacrylate, propyl methacrylate and butyl methacrylate. These comonomers are used singly or in combination of two or more.

The compound (1) of the present invention can be homopolymerized to form a homopolymer.

As polymerization methods for producing the above homopolymer and copolymers, a wide variety of known methods can be employed insofar as a desired polymer is obtained. Examples thereof include radical polymerizations such as bulk polymerization, solution polymerization, suspension polymerization, emulsion polymerization and electronic polymerization; and ion polymerizations such as cationic polymerization and anionic polymerization.

The compound (1) of the invention can form a graft polymer having UV absorptivity by a reaction between the compound and a polymer graft-polymerizable therewith. Preferable examples of the polymers graft-polymerizable with the compound (1) of the invention include polyolefins such as polyethylene, polypropylene, ethylene-propylene copolymer, etc.

The graft polymerization of the compound (1) with the polymer graft-polymerizable therewith can be conducted in a known manner. For example, the compound (1) of the invention may be reacted with the above polymer in the presence of an azo-type radical generating agent such as azobisisobutylonitrile or a peroxide such as di-tert-butyl peroxide, tert-butyl hydroperoxide or methyl ethyl ketone peroxide. A reaction vessel used herein is not limited insofar as a desired graft polymer is obtained. It may be a general-purpose glass or metal vessel, an extruder or a knead-molding machine. Alternatively, a desired graft polymer can be formed by irradiating a mixture of the compound (1) of the invention and the polymer with high-energy beams such as electron beam, γ-rays or the like.

The copolymer or the graft polymer obtained by copolymerizing the compound (1) of the invention with a copolymerizable comonomer as such can be formed, as a weatherable polymer, into film, paint, fibers, molded product or the like, or can be added to other polymers as an addition-type UV absorber.

When the copolymer obtained by copolymerizing the compound (1) of the invention with a copolymerizable comonomer as such is used for forming into film, paint, fibers, molded product or the like as a weatherable polymer, it is preferable that the content of the compound (1) of the invention is in the range of 0.01 to 30% by weight and the copolymer has a weight average molecular weight of, usually 2,000 to 1,000,000, preferably 5,000 to 500,000. When the content of the compound (1) of the invention is less than 0.01% by weight, the weatherability of polymer is likely to be insufficient. When it exceeds 30% by weight, the mechanical properties of the polymer are likely to be impaired.

The compound (1) of the invention can be singly polymerized to form a homopolymer. However, when it is used singly, properties required for processing materials are unsatisfactory. Further, when it is used as an addition-type UV absorber in other polymers, compatibility is insufficient. Accordingly, when the copolymer obtained by copolymerizing the compound (1) of the invention with a copolymerizable comonomer is used as an addition-type UV absorber, it is preferred that the content of the compound (1) of the invention in the copolymer is in the range of 0.05 to 70% by weight and the weight average molecular weight of the copolymer is usually between 2,000 and 1,000,000, preferably between 5,000 and 500,000. When the content of the compound (1) of the invention is less than 0.05% by weight, the weatherability of polymer is likely to be unsatisfactory. When it exceeds 70% by weight, the compatibility with the polymer is likely to be impaired.

Further, when the copolymer obtained by copolymerizing the compound (1) of the invention with a copolymerizable comonomer is added to a polymer compatible therewith, it is advisable that the content of the compound (1) unit of the invention in polymer composition after addition and dissolution is preferably in the range of 0.01 to 30% by weight.

The polymer of the invention and the polymer composition containing the same can be used in combination with other additives, as required, such as light stabilizer, antioxidant, flame retardant, antistatic agent, plasticizer, filler, pigment, coloring agent and the like.

Since the polymer of the invention and the polymer composition containing the same have excellent UV absorptivity, they exhibit outstanding performance especially in applications requiring high weatherability.

The polymer of the invention and the polymer composition containing the same can be molded by known molding methods for conventional polymers, such as injection molding, extrusion molding, blow molding, biaxial centrifugal blow molding, press molding, melt spinning or the like. Further, the polymer and the composition can be used as a solution, dispersion or emulsion in an appropriate solvent or aqueous system to formulate a coating composition, or can also be used as added to a powder coating composition after removing the solvent.

Since the molded product obtained from the polymer. of the invention or the polymer composition containing the same has high weatherability, it exhibits remarkable performance especially in the applications directly exposed to UV or the sunlight, for example, building materials, lamp covers of automobiles or traffic light, car port, sound barrier, agricultural and industrial films or sheets composed of polyester, polycarbonate, vinyl chloride resin or the like, weatherable coating composition for automobiles and outer wall, coating on glass plates, polymer films or polymer sheets, weatherable fibers, etc.

Molded products such as packaging material, container, fibers, film, sheet and the like, which are obtained by blending or coating the polymer of the invention or the polymer composition containing the same have excellent UV absorptivity and can be used preferably in the fields requiring the protection of the contents, the eyes or the like by cutting off the UV.

BEST MODE FOR CARRYING OUT THE INVENTION

The following Synthesis Examples, Examples, Comparative Examples and Test Examples illustrate the invention in further detail. In the following Examples, "parts" and "%" indicate "parts by weight" and "% by weight", respectively.

SYNTHESIS EXAMPLE 1

2-(2'-Hydroxy-5'-methylphenyl)-2H-benzotriazole (22.5 g, 0.1 mols), 5.2 g of 80% paraformaldehyde and 11.0 g (0.15 mols) of diethylamine were dissolved in 25 ml of n-butanol, and the solution was heat-refluxed at 105° C. for 24 hours. After the completion of the reaction, the solvent and the remaining starting material were recovered under reduced pressure to obtain 31.3 g of desired 2-(3'-N,N-diethylaminomethyl-2'-hydroxy-5'-methylphenyl)-2H-benzotriazole as a brown oil (yield 96.9%, purity 96.0%).

$^1$H-NMR (CDCl$_3$): δ=1.09 (t, 6H, CH$_3$), 2.32 (s, 3H, CH$_3$), 2.65 (q, 4H, N—CH$_2$), 3.85 (s, 2H, Ar—CH$_2$—N), 6.97 (s, 1H, Ar—H), 7.41 (m, 2H, Ar—H), 7.55 (s, 1H, Ar—H), 7.97 (m, 2H, Ar—H)

SYNTHESIS EXAMPLE 2

Ten grams (30.9 mmols) of crude 2-(3'-N,N-diethylaminomethyl-2'-hydroxy-5'-methylphenyl)-2H-benzotriazole obtained following the procedures of Synthesis Example 1 and 10.0 g (30.9 mmols) of 2-(2'- hydroxy-5'-methacryloyloxyethylphenyl)-2H-benzotriazole were dissolved in 64 ml of xylene, and 1.5 ml of a 28% sodium methylate•methanol solution were added thereto. The mixture was then refluxed in a nitrogen stream for 10 hours. After the completion of the reaction, the reaction mixture was cooled to room temperature. Yellow crystals precipitated at this stage were separated through filtration, and recrystallized from chloroform to obtain 12.4 g of 6-(2H-benzotriazol-2-yl)-4-methacryloyloxyethyl-2-[3'-(2H-benzotriazol-2-yl)-2'-hydroxy-5'-methylphenyl] methylphenol (hereinafter abbreviated as "RUVA-1") as white crystals (yield 70.7%, purity 98.6%).

$^1$H-NMR (CDCl$_3$): δ=1.86 (s, 3H, CH$_3$), 2.35 (s, 3H, CH$_3$), 2.99 (t, 2H, CH$_2$), 4.26 (s, 2H, CH$_2$), 4.37 (t, 2H, CH$_2$O), 5.45 (t, 1H, vinyl), 6.40 (s, 1H, vinyl), 7.13 (d, 1H, Ar—H), 7.20 (d, 1H, Ar—H), 7.48 (m, 4H, Ar—H), 7.93 (m, 4H, Ar—H), 8.11 (d, 1H, Ar—H), 8.21 (d, 1H, Ar—H), 11.48 (s, 1H, Ar—OH), 11.61 (s, 1H, Ar—OH)

SYNTHESIS EXAMPLE 3

Ten grams (30.9 mmols) of crude 2-(3'-N,N-diethylaminomethyl-2'-hydroxy-5'-methylphenyl)-2H-benzotriazole obtained following the procedures of Synthesis Example 1 and 11.1 g (31.0 mmols) of 5-chloro- 2-(2'-hydroxy-5'-methacryloyloxyethylphenyl)-2H-benzotriazole were dissolved in 64 ml of xylene, and 1.5 ml of a 28% sodium methylate•methanol solution were added thereto. The mixture was then refluxed in a nitrogen stream for 10 hours. After the completion of the reaction, the reaction mixture was cooled to room temperature. Yellow crystals precipitated at this stage were separated through filtration, and recrystallized from chloroform to obtain 13.1 g of 6-(4-chloro-2H-benzotriazol-2-yl)-4-methacryloyloxyethyl-2-[3'-(2H-benzotriazol-2-yl)-2'-hydroxy-5'-methylphenyl] methylphenol (hereinafter abbreviated as "RUVA-2" as white crystals (yield 70.3%, purity 98.8%).

$^1$H-NMR (CDCl$_3$): δ=1.86 (s, 3H, CH$_3$), 2.35 (s, 3H, CH$_3$), 2.99 (t, 2H, CH$_2$), 4.26 (s, 2H, CH$_2$), 4.37 (t, 2H, CH$_2$O), 5.45 (t, 1H, vinyl), 6.04 (s, 1H, vinyl), 7.19 (d, 1H, Ar—H), 7.23 (d, 1H, Ar—H), 7.46 (m, 3H, Ar—H), 7.88 (dd, 1H, Ar—H), 7.94 (m, 3H, Ar—H), 8.06 (d, 1H, Ar—H), 8.18 (d, 1H, Ar—H), 11.47 (s, 1H, Ar—OH), 11.60 (s, 1H, Ar—OH)

SYNTHESIS EXAMPLE 4

Ten grams (30.9 mmols) of crude 2-(3'-N,N-diethylaminomethyl-2'-hydroxy-5'-methylphenyl)-2H-benzotriazole obtained following the procedures of Synthesis Example 1 and 10.5 g (31.1 mmols) of 2-(2'- hydroxy-5'-methacryloyloxypropylphenyl)-2H-benzotriazole were dissolved in 64 ml of xylene, and 1.5 ml of a 28% sodium methylate•methanol solution were added thereto. The mixture was then refluxed in a nitrogen stream for 10 hours. After the completion of the reaction, the reaction mixture was cooled to room temperature. Yellow crystals precipitated at this point were separated through filtration, and recrystallized from chloroform to obtain 12.8 g of 6-(2H-benzotriazol-2-yl)-4-methacryloyloxypropyl-2-[3'-(2H-benzotriazol-2-yl)-2'-hydroxy-5'-methylphenyl] methylphenol (hereinafter abbreviated as "RUVA-3") as white crystals (yield 71.0%, purity 98.6%).

$^1$H-NMR (CDCl$_3$): δ=1.86 (s, 3H, CH$_3$), 2.05 (qui, 2H, CH$_2$), 2.35 (s, 3H, CH$_3$), 2.82 (t, 2H, CH$_2$), 3.05 (t, 2H, CH$_2$), 4.27 (s, 2H, CH$_2$), 4.30 (t, 2H, CH$_2$O), 5.45 (t, 1H, vinyl), 6.04 (s, 1H, vinyl), 7.13 (d, 1H, Ar—H), 7.20 (d, 1H, Ar—H), 7.48 (m, 4H, Ar—H), 7.93 (m, 4H, Ar—H), 8.11 (d, 1H, Ar—H), 8.21 (d, 1H, Ar—H), 11.48 (s, 1H, Ar—OH), 11.61 (s, 1H, Ar—OH)

SYNTHESIS EXAMPLE 5

Ten grams (30.9 mmols) of crude 2-(3'-N,N-diethylaminomethyl-2'-hydroxy-5'-methylphenyl)-2H-benzotriazole obtained following the procedures of Synthesis Example 1 and 9.57 g (30.9 mmols) of 2-(2'- hydroxy-5'-acryloyloxyethylphenyl)-2H-benzotriazole were dissolved in 64 ml of xylene, and 1.5 ml of a 28% sodium methylate•methanol solution were added thereto. The mixture was then refluxed in a nitrogen stream for 10 hours. After the completion of the reaction, the reaction mixture was cooled to room temperature. Yellow crystals precipitated at this stage were separated through filtration, and recrystallized from chloroform to obtain 11.8 g of 6-(2H-benzotriazol-2-yl)-4-acryloyloxyethyl-2-[3'-(2H-benzotriazol-2-yl)-2'-hydroxy-5'-methylphenyl] methylphenol (hereinafter abbreviated as "RUVA-4") as white crystals (yield 69.1%, purity 99.0%).

$^1$H-NMR (CDCl$_3$): δ=2.35 (s, 3H, CH$_3$), 3.04 (t, 2H, CH$_2$), 4.26 (s, 2H, CH$_2$), 4.42 (t, 2H, CH$_2$O), 5.82 (dd, 1H, vinyl), 6.12 (dd, 1H, vinyl), 6.41 (dd, 1H, vinyl), 7.14 (d, 1H, Ar—H), 7.21 (d, 1H, Ar—H), 7.47 (m, 4H, Ar—H), 7.92 (m, 4H, Ar—H), 8.12 (d, 1H, Ar—H), 8.20 (d, 1H, Ar—H), 11.49 (s, 1H, Ar—OH), 11.61 (s, 1H, Ar—OH)

SYNTHESIS EXAMPLE 6

2-(2'-Hydroxy-5'-methylphenyl)-2H-benzotriazole (45.1 g, 0.2 mols), 64.7 g (0.2 mols) of 2-(2'-hydroxy-5'-methacryloyloxyethylphenyl)-2H-benzotriazole, 11.6 g (0.2 mols) of acetone and 12 ml of conc. hydrochloric acid were stirred in a nitrogen stream at 40° C. for 5 ours. The reaction mixture was subjected to silica gel column chromatography to obtain 22.1 g of 6-(2H-benzotriazol-2-yl)-4-methacryloyloxyethyl-2-[3'-(2H-benzotriazol-2-yl)-2'-hydroxy-5'-methylphenyl]-α,α-dimethylmethylphenol (hereinafter abbreviated as "RUVA-5") as white crystals (yield 18.8%, purity 99.0%).

$^1$H-NMR (CDCl$_3$): δ=1.68 (s, 6H, CH$_3$), 1.85 (s, 3H, CH$_3$), 2.35 (s, 3H, CH$_3$), 2.98 (t, 2H, CH$_2$), 4.37 (t, 2H, CH$_2$O), 5.45 (t, 1H, vinyl), 6.04 (s, 1H, vinyl), 7.11 (d, 1H, Ar—H), 7.18 (d, 1H, Ar—H), 7.48 (m, 4H, Ar—H), 7.93 (m, 4H, Ar—H), 8.09 (d, 1H, Ar—H), 8.19 (d, 1H, Ar—H), 11.47 (s, 1H, Ar—OH), 11.60 (S, 1H, Ar—OH)

SYNTHESIS EXAMPLE 7

A mixture consisting of 30 g of RUVA-1 obtained following the procedures of Synthesis Example 2, 70 g of methyl methacrylate and 2.8 g of azobisisobutyronitrile was gradually added dropwise to 100 g of dimethylformamide heated at 120° C. in a glass flask fitted with a condenser, a nitrogen introduction tube, a thermometer, a dropping funnel and a stirrer, and the mixture was further maintained at the same temperature for 4 hours. The resulting reaction solution was poured into excess methanol. The solids precipitated were collected through filtration, and dried in vacuo at 40° C. for 15 hours to obtain 98 g of a pale yellow powdery polymer. The GPC analysis of the polymer based on standard polystyrene revealed that the weight average molecular weight was 10,200. Further, from the $^1$H-NMR analysis and the absorbance in the maximum absorption wavelength, the polymer was found to be a copolymer of RUVA-1 and methyl methacrylate, containing and RUVA-1 contained in an amount of 30% by weight based on the copolymer composition.

SYNTHESIS EXAMPLE 8

A copolymer of RUVA-2, RUVA-3, RUVA-4 or RUVA-5 and methyl methacrylate shown in Table 1 was obtained under the same conditions as in Synthesis Example 7 except that RUVA-2, RUVA-3, RUVA-4 or RUVA-5 was used instead of RUVA-1.

TABLE 1

| RUVA used | Yield (g) | Weight average molecular weight | RUVA content (%) |
| --- | --- | --- | --- |
| RUVA-2 | 96 | 10,100 | 30 |
| RUVA-3 | 97 | 10,400 | 30 |
| RUVA-4 | 98 | 10,200 | 31 |
| RUVA-5 | 97 | 10,300 | 30 |

SYNTHESIS EXAMPLE 9

A glass flask fitted with a condenser, a nitrogen introduction tube, a thermometer, a dropping funnel and a stirrer was charged with 75 g of RUVA-1 obtained in Synthesis Example 2, 125 g of methyl methacrylate, 50 g of 2-ethylhexyl acrylate, 5.0 g of acrylic acid, 0.5 g of triallylamine, 10 g of Aqualon RN-50 (copolymerizable emulsion, product of Dai-ichi Kogyo Seiyaku Co., Ltd.) and 400 g of water. The mixture was stirred at 70° C. for 30 minutes while introducing nitrogen to emulsify the system. While being stirred at 70° C., a 1% ammonium persulfate aqueous solution was added thereto dropwise over the course of 2 hours. After the completion of the dropwise addition, the reaction mixture was further stirred for 3 hours for ageing to obtain 790 g of an aqueous emulsion-type high-molecular UV absorber (solid content—33.5%, content of the UV absorber (RUVA-l) in the solid—28%).

EXAMPLE 1

Seventy parts of commercially available methyl polymethacrylate and 30 parts of the polymer obtained in Synthesis Example 7 were dissolved in 500 parts of 1,1,2,2-tetrachloroethane, and the solution was coated on a circular quartz plate with a diameter of 30 mm using a spinner. The resulting coated film was air-dried for 1 hour, and then dried under reduced pressure at 60° C. for 12 hours to form on the circular quartz plate a uniform thin film with a thickness of approximately 1 μm. The thin film contained 9% of RUVA-1 obtained in Synthesis Example 2.

EXAMPLE 2

A quartz plate having formed thereon a polymethyl methacrylate coating containing 30% of a copolymer of each RUVA and methyl methacrylate was obtained under the same conditions as those used in Example 1 except that the polymer obtained in Synthesis Example 8 was used instead of the polymer obtained in Synthesis Example 7. The content of each RUVA unit in the copolymer was 9%.

COMPARATIVE EXAMPLE 1

Commercially available polymethyl methacrylate (91 parts) and 9 parts of 2-(2'-hydroxy-5'-methylphenyl) benzotriazole (hereinafter abbreviated as "comparative UVA-1") were dissolved in 500 parts of 1,1,2,2-tetrachloroethane, and the solution was coated on a circular quartz plate with a diameter of 30 mm using a spinner. The resulting coated film was air-dried for 1 hour, and then dried under reduced pressure at 60° C. for 12 hours to form on the circular quartz plate a uniform thin film containing 9% of comparative UVA-1 with a thickness of approximately 1 $\mu$m.

COMPARATIVE EXAMPLE 2

Commercially available polymethyl methacrylate (91 parts) and 9 parts of 2-(2'-hydroxy-3',5'-di(tert-butyl)phenyl] benzotriazole (hereinafter abbreviated as "comparative UVA-2") were dissolved in 500 parts of 1,1,2,2-tetrachloroethane, and the solution was coated on a circular quartz plate with a diameter of 30 mm using a spinner. The resulting coated film was air-dried for I hour, and then dried under reduced pressure at 60° C. for 12 hours to form on the circular quartz plate a uniform thin film containing 9% of comparative UVA-2 with a film thickness of approximately 1 $\mu$m.

TEST EXAMPLE 1

The polymethyl methacrylate coated quartz plate obtained in Example 1, Example 2, Comparative Example 1 or Comparative Example 2 was dipped in hot water of 70° C., and an absorbance of the film at 340 nm was measured at fixed time intervals.

$$\text{Absorbance retention (\%)} = \frac{\text{absorbance after 10 hours}}{\text{initial absorbance}} \times 100$$

The absorbance retention after 10 hours or 40 hours in Example 1, Example 2, Comparative Example 1 and Comparative Example 2 is shown in Table 2.

TABLE 2

|  | RUVA or UVA | Absorbance retention (%) | |
|---|---|---|---|
|  |  | after 10 hours | after 40 hours |
| Example 1 | RUVA-1 | 99 | 99 |
| Example 2 | RUVA-2 | 100 | 99 |
|  | RUVA-3 | 99 | 99 |
|  | RUVA-4 | 99 | 99 |
|  | RUVA-5 | 100 | 100 |
| Comparative Example 1 | Comparative UVA-1 | 5 | 0 |
| Comparative Example 2 | Comparative UVA-2 | 80 | 24 |

It was found that in Comparative Examples 1 and 2 containing the addition-type UV absorbers, the absorbance of the film is almost linearly decreased by the elution thereof, whereas the polymethyl methacrylate resin film containing the copolymer having the UV absorption in the present invention retains almost the initial absorbance without the elution of the UV absorber.

EXAMPLE 3

One hundred parts of a thermoplastic acrylic emulsion (solid content—41.5%) were mixed with 30 parts of the aqueous emulsion-type high-molecular UV absorber obtained in Synthesis Example 9. The mixture was cast-coated on a polycarbonate plate or a glass plate with a thickness of 3 mm, air-dried at room temperature, and then dried under reduced pressure at 60° C. for 12 hours to form on the polycarbonate plate or the glass plate a uniform thin film containing 5.5% of RUVA-1 with a film thickness of approximately 25 $\mu$m.

COMPARATIVE EXAMPLE 3

One hundred parts of a thermoplastic acrylic emulsion (solid content—41.5%) were mixed with 2.4 parts of comparative UVA-1. The mixture was cast-coated on a polycarbonate plate or a glass plate with a thickness of 3 mm, air-dried at room temperature, and then dried under reduced pressure at 60° C. for 12 hours to form on the polycarbonate plate or the glass plate a uniform thin film containing 5.5% of comparative UVA-1 with a film thickness of approximately 25 $\mu$m.

TEST EXAMPLE 2

The thermoplastic acrylic emulsion-coated polycarbonate plate obtained in Example 3 or Comparative Example 3 was subjected to an accelerated weathering test for 1,200 hours using a Dew cycle sunshine Super Long-Life Weather Meter WEL-SUN-DC (product of Test Instruments Co. Ltd., 18-minute rainfall every 120 minutes). Then, a yellow index ($\Delta$YI) was measured. The results are shown in Table 3.

TABLE 3

|  | Yellow index after 1,200 hours ($\Delta$YI) |
|---|---|
| Example 3 | 0.3 |
| Comparative Example 3 | 11.4 |

It was found that the thermoplastic acrylic emulsion-coated polycarbonate plate containing the addition-type UV absorber in Comparative Example 3 was distinctly and drastically yellowed with the lapse of time during the weathering test period of time, whereas the emulsion film having the UV absorption in the present invention effectively absorbed the UV over a long period of time, showing a very high weatherability with almost no yellowing of the polycarbonate substrate.

TEST EXAMPLE 3

The thermoplastic acrylic emulsion-coated glass plate obtained in Example 3 or Comparative Example 3 was allowed to stand in a 5 w/v% sodium carbonate aqueous solution of 40° C. for 10 days, and the yellow index ($\Delta$YI) was then measured. The results are shown in Table 4.

TABLE 4

| | Yellow index after allowed to stand for 10 days (ΔYI) |
|---|---|
| Example 3 | 0.1 |
| Comparative Example 3 | 10.5 |

It was found that the thermoplastic acrylic emulsion-coated glass plate containing the additive-type UV absorber in Comparative Example 3 was clearly yellowed drastically after it was allowed to stand in the 5 w/v% sodium carbonate aqueous solution for 10 days, whereas the emulsion film having the UV absorption in the present invention was little yellowed, showing quite a high alkali resistance.

TEST EXAMPLE 4

The thermoplastic acrylic emulsion-coated glass plate obtained in Example 3 or Comparative Example 3 was allowed to stand in water of 40° C. containing a copper powder for 10 days. The yellow index (ΔYI) was then measured. The results are shown in Table 5.

TABLE 5

| | Yellow index after allowed to stand for 10 days (ΔYI) |
|---|---|
| Example 3 | 1.8 |
| Comparative Example 3 | 108 |

It was found that the thermoplastic acrylic emulsion-coated glass plate containing the addition-type UV absorber in Comparative Example 3 was clearly yellowed drastically after it was allowed to stand in water containing a copper powder for 10 days, whereas the emulsion film having the UV absorption in the present invention was little yellowed, showing quite a high metal ion resistance.

EXAMPLE 4

A curable paint prepared by mixing 4.0 g of Art Resin UN-3320HA (polyurethane acrylate-type oligomer, product of Negami Kogyo K.K.), 3.0 g of pentaerythritol triacrylate, 3.0 g of dipentaerythritol hexacrylate, 0.3 g of DaRocuR1173 (polymerization initiator, product of Ciba Geigy AG), 1.0 g of methyl ethyl ketone and 0.3 g of RUVA-4 obtained following the procedures of Synthesis Example 5 was coated on a polycarbonate plate with a thickness of 3 mm to a film thickness of 5 μm using a bar coater, and dried for 15 minutes using a circulating hot-air drier of 70° C. Subsequently, irradiation was conducted in air at a line speed of 2 m/min using a high-pressure mercury lamp (80 w/cm) to form a UV cured coated film.

COMPARATIVE EXAMPLE 4

A curable paint prepared by mixing 4.0 g of Art Resin UN-3320HA (polyurethane acrylate-type oligomer, product of Negami Kogyo K.K.), 3.0 g of pentaerythritol triacrylate, 3.0 g of dipentaerythritol hexacrylate, 0.3 g of DaRocuR1173 (polymerization initiator, product of Ciba Geigy AG), 1.0 g of methyl ethyl ketone and 0.3 g of comparative UVA-2 was coated on a polycarbonate plate with a thickness of 3 mm to a film thickness of 5 μm using a bar coater, and dried for 15 minutes using a circulating hot-air drier of 70° C. Subsequently, irradiation was conducted in air at a line speed of 2 m/min using a high-pressure mercury lamp (80 w/cm) to form a UV cured coated film.

TEST EXAMPLE 3

The UV cured coated polycarbonate plates obtained in Example 4 and Comparative Example 4 were compared with respect to a pencil hardness, a resistance to rub damage, an adhesion and a weatherability (1) Pencil hardness:
  Measured according to JIS K-5400.

(2) Resistance to rub damage
  A degree of damage was evaluated using a #0000 steel wool based on the following criteria.
  A: The plate is not damaged or little damaged even though strongly rubbed.
  B: The plate is damaged when strongly rubbed.
  C: The plate is damaged (3) Adhesion:
  One hundred crosscuts (1 mm×1 mm) were applied to the coated film, and a cellophane tape was adhered thereto. Then, the tape was abruptly peeled off therefrom perpendicularly, and the adhesion of the coated film was evaluated according to the following criteria.
  ○: No peeling-off is observed
  ×: Peeling-off is partially observed.

(4) Weatherability:
  The condition of the coated film was observed after it was subjected to an accelerated weathering test for 2,000 hours using a Dew cycle sunshine Super Long-Life Weather Meter WEL-SUN-DC (product of Test Instruments Co., Ltd., 18-minute rainfall every 120 minutes), and the yellow index (ΔYI) was evaluated. The condition of the coated film was evaluated according to the following criteria.
  ○: The coated film is unchanged.
  Δ: The coated film is cracked.
  ×: The coated film is spontaneously peeled off completely.

The results are shown in Table 6.

TABLE 6

| | UVA | Pencil hardness | Resistance to rub damage | Adhesion | Weatherability (condition, ΔYI) 1,000 hrs | 2,000 hrs |
|---|---|---|---|---|---|---|
| Example 3 | RUVA-4 | 4H | A | ○ | ○, 0.3 | ○, 1.0 |
| Comparative Example 3 | Comparative UVA-2 | 2H | A | ○ | ○, 9.5 | Δ, 15.3 |

The UV cured coated film containing comparative UVA-2 in Comparative Example 3 had an adverse effect on the UV curing reaction because comparative UVA-2 was an addition-type UV absorber, and the hardness of the coated film was slightly decreased. Further, the UV cured coated polycarbonate plate containing the comparative UVA-2 distinctly and drastically yellowed with the lapse of time during the weathering test period of time owing to the decrease in the UV absorption of the coated film caused by the bleedout of comparative UVA-2 with time. On the other hand, the reactive UV absorber of the present invention was reacted with the other UV curable monomer by the UV curing reaction, and incorporated into the cured film through the covalent bond, with the result that the hardness of the coated film was high and the weatherability of the coated film itself was also high. Further, in the UV cured coated film containing the reactive UV absorber of the present invention, the UV absorber did not bleed out. Accordingly, it absorbed UV effectively over a long period of time, and the polycarbonate substrate hardly yellowed, showing a very high weatherability.

EXAMPLE 5

The molar absorption coefficients in the maximum absorption wavelength of 2-(2'-hydroxy-5'-methacryloyloxyethylphenyl)-2H-benzotriazole as a starting material of RUVA-1 formed in Synthesis Example 2, 2-(2'-hydroxy-5'-methylphenyl)-2H-benzotriazole (used in Synthesis Example 1) as a starting material of the above-mentioned compound and 2-[2'-hydroxy-3',5'-di(dimethylbenzyl)phenyl]benzotriazole (hereinafter abbreviated as "comparative UVA-3") known as a general sparingly volatile benzotriazole-type UV absorber were as low as 17,600, 16,400 and 15,400 [L-mol$^{-1}$·cm$^{-1}$] respectively, whereas that of RUVA-1 formed in Synthesis Example 2 was 33,400 [L-mol$^{-1}$·cm$^{-1}$] which was quite high. RUVA-1 was found to have a markedly high UV absorption compared with the other UV absorbers.

TABLE 7

| UVA | Molar absorption coefficient [L.mol$^{-1}$.cm$^{-1}$] |
|---|---|
| 2-(2'-hydroxy-5'-methacryloyloxyethylphenyl)-2H-benzotriazole | 17,600 |
| 2-(2'-hydroxy-5'-methylphenyl)-2H-benzotriazole | 16,400 |
| Comparative UVA-3 | 15,400 |
| RUVA-1 | 33,400 |

What is claimed is:

1. An ultraviolet ray absorber comprising a 2,2'-bis(6-benzotriazolylphenol) compound represented by the formula

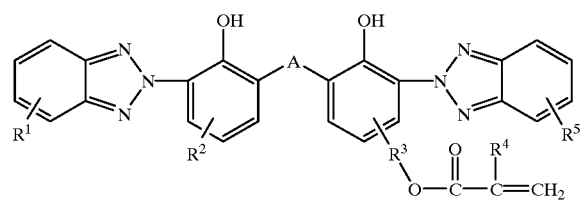

wherein

A represents a single bond, a methylene group, —CH(CH$_3$)—, —C(CH$_3$)$_2$— or —C(CH$_3$)(C$_2$H$_5$)—, R$^1$ and R$^5$ are the same or different, and each represents a hydrogen atom, an alkyl group having 1 to 4 carbon atoms, an aryl group, an alkoxy group having 1 to 4 carbon atoms or a halogen atom, R$^2$ represents a hydrogen atom or an alkyl group having 1 to 8 carbon atoms, R$^3$ represents a single bond or a linear or branched alkylene group having 1 to 6 carbon atoms, and R$^4$ represents a hydrogen atom or a methyl group.

2. A copolymer comprising 0.01 to 70% by weight of a 2,2'-bis(6-benzotriazolylphenol) compound claim 1 as a copolymerizable compound and having a weight average molecular weight of 2,000 to 1,000,000.

3. The copolymer according to claim 2, which comprises a 2,2'-bis(6-benzotriazolylphenol) compound as defined in claim 1 and a vinyl monomer, the amount of 2,2'-bis(6-benzotriazolylphenol) compound as the copolymerizable component being in the range of 0.01 to 70% by weight, the copolymer having a weight average molecular weight of 2,000 to 1,000,000.

4. The copolymer according to claim 2, which comprises a 2,2'-bis(6-benzotriazolylphenol) compound as defined in claim 1 and a vinyl monomer, the amount of the 2,2'-bis(6-benzotriazolylphenol) compound as the copolymerizable component being in the range of 0.01 to 30% by weight, the copolymer having a weight average molecular weight of 2,000 to 1,000,000.

5. The copolymer according to claim 2, which comprises a 2,2'-bis(6-benzotriazolylphenol) compound as defined in claim 1 and a vinyl monomer, the amount of 2,2'-bis(6-benzotriazolylphenol) compound as the copolymerizable component being in the range of 0.05 to 70% by weight, the copolymer having a weight average molecular weight of 2,000 to 1,000,000.

6. The copolymer according to claim 3, 4 or 5, wherein the vinyl monomer is at least one species selected from the group consisting of styrene, methylstyrene, acrylate ester, methacrylate ester, acrylamide, acrylonitrile, methacrylonitrile, vinyl acetate, vinylidene chloride, vinyl chloride, ethylene, propylene, butadiene, isoprene, octene, decene and dodecene.

* * * * *

UNITED STATES PATENT AND TRADEMARK OFFICE
CERTIFICATE OF CORRECTION

PATENT NO. : 6,281,313 B1
DATED : August 28, 2001
INVENTOR(S) : Nakano et al.

It is certified that error appears in the above-identified patent and that said Letters Patent is hereby corrected as shown below:

Column 1,
Line 35, "it" should read -- It --
Line 40, "ions(metal" should read -- ions (metal --

Column 2,
Line 22, "the," should read -- the --

Column 5,
Line 42, "-2 '-" should read -- -2'- --

Column 6,
Line 5, "- 2'-" should read -- -2'- --

Column 13,
Line 66, "Hydroxy" should read -- hydroxy --

Column 15,
Line 47, "Hydroxy" should read -- hydroxy --

Column 16,
Line 49, "ageing" should read -- aging --

Column 22,
Line 20, "compound claim 1" should read -- compound as defined in claim 1 --

Signed and Sealed this

Thirteenth Day of August, 2002

Attest:

JAMES E. ROGAN
Attesting Officer     Director of the United States Patent and Trademark Office